United States Patent
Yang et al.

(10) Patent No.: US 12,128,015 B2
(45) Date of Patent: Oct. 29, 2024

(54) APE/REF1 INHIBITORS FOR THE TREATMENT OF CANCER

(71) Applicants: Chapman University, Orange, CA (US); The Regents of the University of California, Oakland, CA (US)

(72) Inventors: Sun Yang, Orange, CA (US); Keykavous Parang, Orange, CA (US); Richard Chamberlin, Irvine, CA (US); Frank L Meyskens, Jr., Orange, CA (US)

(73) Assignees: Chapman University, Orange, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 17/990,401

(22) Filed: Nov. 18, 2022

(65) Prior Publication Data

US 2023/0157978 A1    May 25, 2023

Related U.S. Application Data

(60) Provisional application No. 63/281,517, filed on Nov. 19, 2021.

(51) Int. Cl.
*A61P 35/00* (2006.01)
*A61K 31/165* (2006.01)

(52) U.S. Cl.
CPC ............ *A61K 31/165* (2013.01); *A61P 35/00* (2018.01)

(58) Field of Classification Search
CPC .............................. A61K 31/165; A61P 35/00
See application file for complete search history.

(56) References Cited

FOREIGN PATENT DOCUMENTS

SU          339154 A    *    1/1976

OTHER PUBLICATIONS

Liu X, Shen Z, Wang T, Liu M. Sensitive and photo-triggered transformation of hierarchical helices assembled from achiral bolaamphiphiles. J Colloid Interface Sci. Dec. 1, 2014;435:1-7. doi: 10.1016/j.jcis.2014.08.014. Epub Aug. 23, 2014. PMID: 25200725. (Year: 2014).*

(Continued)

*Primary Examiner* — Deepak R Rao
*Assistant Examiner* — Kevin S Martin
(74) *Attorney, Agent, or Firm* — K&L Gates LLP; Louis C. Cullman; Giorgios N. Kefallinos

(57) ABSTRACT

Apurinic/apuyrimidinic endonuclease 1/Redox Factor-1 (APE/Ref-1) inhibitors are provided along with methods of using the same. The inhibitor has the structure of Formula I:

Formula I

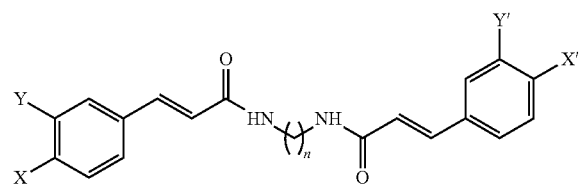

or a pharmaceutically acceptable salt thereof. n is an integer from 4 to 14, X and X' are each independently H or OH, and Y and Y' are each independently H or OH.

16 Claims, 7 Drawing Sheets

(56) References Cited

OTHER PUBLICATIONS

Wang J, Hong G, Li G, Wang W, Liu T. Novel Homo-Bivalent and Polyvalent Compounds Based on Ligustrazine and Heterocyclic Ring as Anticancer Agents. Molecules. Dec. 9, 2019;24(24):4505. doi: 10.3390/molecules24244505. PMID: 31835359; Pmcid: PMC6943434. (Year: 2019).*

Yingyongnarongkul BE, Apiratikul N, Aroonrerk N, Suksamrarn A. Solid-phase synthesis and antibacterial activity of hydroxycinnamic acid amides and analogues against methicillin-resistant *Staphylococcus aureus* and vancomycin-resistant *S. aureus*. Bioorg Med Chem Lett. Nov. 15, 2006;16(22):5870-3. doi: (Year: 2006).*

Loureiro, J.B et al. Targeting p53 for Melanoma Treatment: Counteracting Tumour Proliferation, Dissemination and Therapeutic Resistance. Cancers 2021, 13, 1648. https://doi.org/ 10.3390/cancers13071648 (Year: 2021).*

Hugo J.C. Froufe, Rui M.V. Abreu & Isabel C.F.R. Ferreira (2013) Virtual screening of low molecular weight mushrooms compounds as potential Mdm2 inhibitors, Journal of Enzyme Inhibition and Medicinal Chemistry, 28:3, 569-575, DOI:10.3109/14756366.2012.658787 (Year: 2013).*

Slominski et al. Int J Cancer. Mar. 15, 2009; 124(6): 1470-1477. doi:10.1002/ijc.24005 (Year: 2009).*

Ha JH, Park SN. Dimeric cinnamoylamide analogues for regulation of tyrosinase activity in melanoma cells: A role of diamide-link chain length. Bioorg Med Chem. Dec. 15, 2018;26(23-24):6015-6022. doi: 10.1016/j.bmc.2018.10.036. Epub Nov. 2, 2018. PMID: 30446440. (Year: 2018).*

Yang Z et al. "The role of APE/Ref-1 signaling pathway in hepatocellular carcinoma progression" Int J Oncol. 2014; 45(5):1820-8.

Yang S et al. "Alterations in the expression of the apurinic/apyrimidinic endonuclease-1/redox factor-1 (APE/Ref-1) in human melanoma and identification of the therapeutic potential of resveratrol as an APE/Ref-1 inhibitor" Mol Cancer Ther. 2005; 4(12):1923-35.

Gaiddon C et al. "Ref-1 regulates the transactivation and pro-apoptotic functions of p53 in vivo" The EMBO J 1999; 18(20):5609-21.

* cited by examiner

APE/REF1 INHIBITORS FOR THE TREATMENT OF CANCER

CROSS REFERENCE TO RELATED APPLICATIONS

This application claims the benefit of U.S. Provisional patent application 63/281,517 filed Nov. 19, 2021, the entire contents of which are incorporated by reference herein.

STATEMENT REGARDING FEDERALLY SPONSORED RESEARCH OR DEVELOPMENT

This invention was made with government support under Grant No. K08CA179084 awarded by the National Cancer Institute. The government has certain rights in the invention.

FIELD

The present disclosure relates to compounds that are APE/Ref1 inhibitors, methods of preparing these compounds, and the use of these compounds in the treatment of cancer.

BACKGROUND

Melanoma arising from melanocytes makes up only 2% of all skin cancers, while it causes over 80% of all skin cancer deaths. In recent years, melanoma incidence has increased more rapidly than other cancer types in the United States, and it is expected that 7,180 patients will have died due to melanoma in 2021 alone. Ultraviolet radiation (UVR), which can generate reactive oxygen species (ROS) and nitric oxide (NO) in the skin, has been implicated as a significant environmental contributor to the development of melanoma. The contributions of UVR to melanomagenesis and malignant development may be at least partially due to the ROS- or NO-induced DNA damage, which has been studied in the inventors' laboratory and by other groups.

APE/Ref-1 is a critical enzyme in DNA base excision repair, which catalyzes the cleavage of the phosphodiester bond at either the 5' or 3' end of an apurinic/apyrimidinic site. Studies have also revealed that apurinic/apyrimidinic endonuclease 1 (APE-1) exhibits distinct redox functions that facilitate the DNA binding activities of many nuclear transcription factors (such as AP-1 dimers, Myb, NF-κB, p53, and HIF-α) known as Redox Factor-1 (Ref-1). APE/Ref-1 plays a critical role in malignant transformation when combined with elevated ROS levels in the JB6 model. Notably, the inventors' previous studies demonstrated that APE/Ref-1 is induced by ROS and nitric oxide stress. In addition, genome-wide analyses and proteomic studies also suggested an important role of APE/Ref-1 in regulating many biological processes, such as mitochondrial function and rRNA quality control.

Accumulating evidence shows that many human tumors, including the brain, cervical, and prostate cancers, exhibit elevated APE/Ref-1 expression and abnormal subcellular localization compared to normal tissues, making it an attractive druggable target for developing a new cancer therapeutic strategy. Up-regulated APE/Ref-1 is shown to protect cells from various pro-apoptosis stimuli, including oxidative stresses, chemotherapeutic drugs, and radiation treatment. Elevated APE/Ref-1 was closely associated with increased metastatic potential. Compounds impairing APE/Ref-1-mediated redox signaling or DNA repair activity have shown enhanced anti-tumor activities. The inventors' previous studies demonstrated that over-expressed APE/Ref-1 contributes to tumor development and progression in human melanoma and hepatocellular carcinoma (Yang Z et al. Int J Oncol. 2014; 45(5):1820-8; Yang S et al. Mol Cancer Ther. 2005; 4(12):1923-35). Down-regulation of APE/Ref-1 expression sensitized melanoma cells to induced apoptosis both in vitro and in vivo. Some other studies also showed pro-apoptotic effects of APE/Ref-1 by potentiating p53-mediated signaling (Gaiddon C et al. The EMBO J 1999; 18(20):5609-21). The different experimental stresses applied in the studies might explain the distinct role of APE/Ref-1 in contributing to apoptosis.

In addition, given the complexity of the cancer signaling network, there are wide varieties of intra- and intercellular signaling pathways that could fuel cancer progression. APE/Ref-1 regulates many nuclear transcription factors in a redox-dependent and -independent manner. Inhibition of APE/Ref-1 may generate a much broader inhibition of its regulated downstream signaling rather than only blocking a single pathway, which might be more efficient and minimize the development of drug resistance.

SUMMARY

Human malignant melanoma exhibits imbalanced redox status leading to activation of many redox-sensitive signaling pathways. Induced as an adaptive response to oxidative stress, multifunctional protein APE/Ref-1 serves as a redox chaperone that regulates many nuclear transcription factors and is an important mechanism in cancer cell survival of oxidative stress. The inventors' previous studies showed that knockdown of APE/Ref-1 significantly sensitized melanoma cells to chemotherapy and inhibited their metastatic potential, suggesting APE/Ref-1 is a potential druggable target for melanoma therapy. In the present disclosure, an APE/Ref-1 inhibitor, bis-cinnamoyl-1,12-dodecamethylenediamine (2), exhibiting potent anti-tumor activity was successfully synthesized. In a xenograft mouse model, compound 2 treatment effectively inhibited the tumor growth by 44.7% at a dose of 5 mg/kg after i.p. injection compared to the control group, with no significant systemic toxicity observed. Analogs of lead compound 2 have been synthesized to determine the structure-activity relationship based on their anti-melanoma activities. Among those, 4-hydroxyphenyl derivative (11) exhibited improved water solubility compared to its parental compound 2 with potent anti-melanoma activities. In comparison to other well-studied APE/Ref-1 inhibitors, compound 11 treatment at lower concentrations showed significant inhibition of melanoma proliferation with an $IC_{50}$ less than <0.1 μM. AP-1 is a nuclear transcription factor that binds with APE/Ref-1, which then upregulates the AP-1 transcription activity in a redox-dependent manner. As determined by a luciferase reporter analysis, compound 2 treatment was shown to effectively inhibit $H_2O_2$-activated AP-1 transcription activities. The present disclosure has developed small molecular APE/Ref-1 inhibitors, which exhibited promising anti-melanoma activities both in vitro and in vivo. Thus, targeting APE/Ref-1-mediated signaling using pharmaceutical inhibitors is an effective strategy for melanoma treatment with potentially high impact.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combi- FIG. 1. Molecular docking and binding mode of compound 2 to the druggable binding site of APE/Ref-1 protein (1BIX).

FIG. 2A. Cytotoxicity of compound 2 in A375 melanoma cells; FIG. 2B. Cytotoxicity of compound 2 in human immortalized melanoblasts cells (Hermes 1, 3A, and 4A). The bar represented the average of three independent experiments. FIG. 2C. Cytotoxicity of compound 11 in comparison to APE/Ref-1 inhibitors E2009 and E3330 in A375 melanoma cells. FIG. 2D. Melanoma cells are more sensitive to compound 11 in comparison to melanoblast Hermes 1 cells.

DETAILED DESCRIPTION

Figure 1:
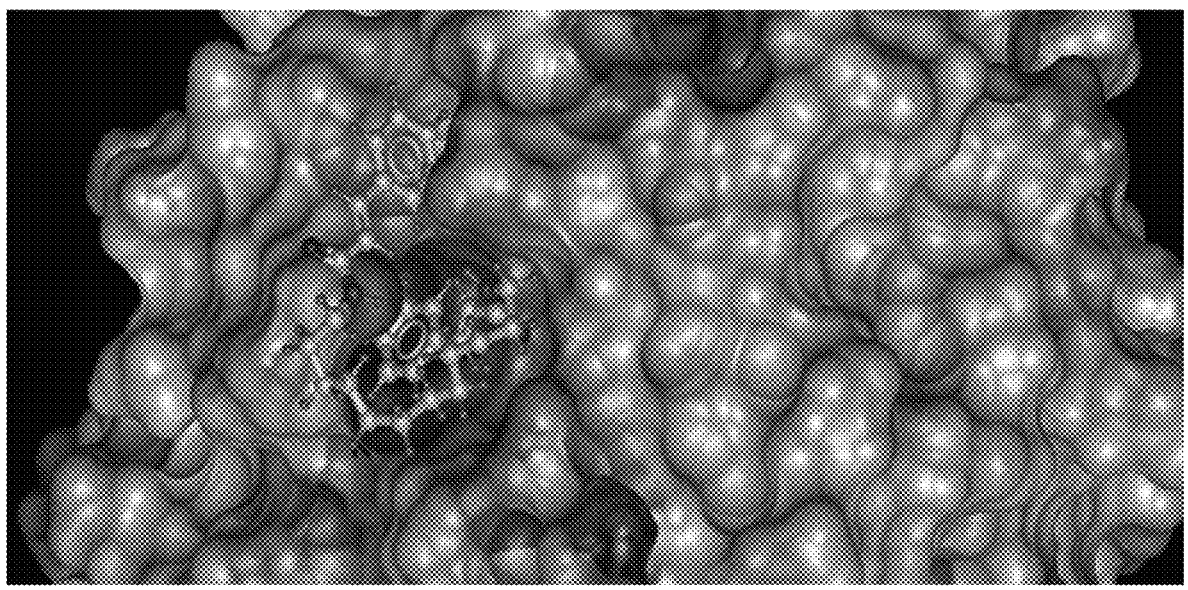

The APE/Ref-1 inhibitors disclosed herein showed promising anti-melanoma activities in vitro and in vivo, suggesting that targeting APE/Ref-1-mediated signaling is an effective strategy for melanoma therapy.

Aspects of the present disclosure are directed to APE/Ref-1 inhibitors having the structure of Formula I:

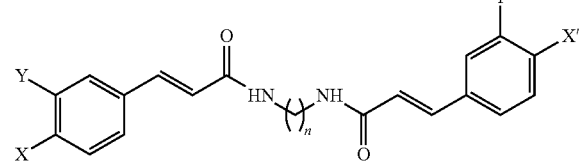

Formula I or a pharmaceutically acceptable salt thereof,
wherein n is an integer from 4 to 14,
X and X' are each independently H or OH, and
Y and Y' are each independently H or OH.
In some embodiments, n is an integer from 6 and 12.
In some embodiments, n is 6.
In some embodiments, n is 12.
In some embodiments, n is 12, X is H, X' is H, Y is H, and Y' is H.
In some embodiments, n is 12, X is OH, X' is OH, Y is H, and Y' is H.
In some embodiments, n is 6, X is OH, X' is OH, Y is H, and Y' is H.
In some embodiments, n is 12, X is H, X' is H, Y is OH, and Y' is OH.
In some embodiments, n is 12, X is H, X' is H, Y is OH, and Y' is H.
In some embodiments, n is 12, X is OH, X' is H, Y is H, and Y' is H.
In some embodiments, n is 6, X is H, X' is H, Y is H, and Y' is H.

Other aspects of the present disclosure are directed to APE/Ref-1 inhibitors having the structure of Formula II:

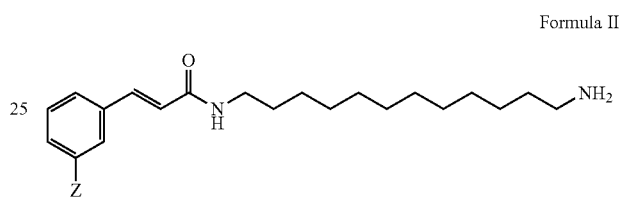

Formula II or a pharmaceutically acceptable salt thereof,
wherein Z is H or OH.
In some embodiments, Z is OH.
In some embodiments, Z is H.

Other aspects of the present disclosure are directed to pharmaceutical compositions that include a compound having the structure of Formula I:

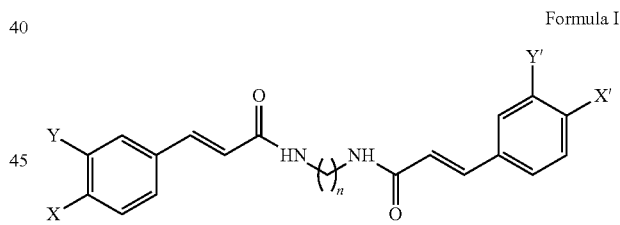

Formula I or a pharmaceutically acceptable salt thereof,
wherein n is an integer from 4 to 14,
X and X' are each independently H or OH, and
Y and Y' are each independently H or OH; or
a compound having the structure of Formula II:

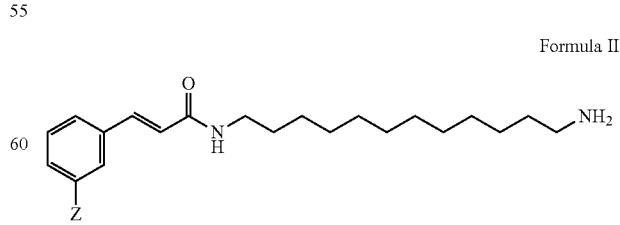

Formula II or a pharmaceutically acceptable salt thereof,
wherein Z is H or OH; or
a combination thereof.

Other aspects of the present disclosure are directed to methods of treating cancer that include administering the foregoing compounds and/or pharmaceutical composition to a subject in need thereof.

In some embodiments, the cancer is melanoma.

The crystal structure of APE/Ref-1 revealed potential druggable pockets in the vicinity of Cys65, which is located in the redox regulation domain. Virtual screenings were conducted using the ICM software package (Molsoft) which docks small molecules from a large database and ranks binding using an energetic scoring function. The chemical structure of the top hit compounds was identified. A series of analogs based on the lead compound structure were synthesized. Among them, bis-cinnamoyl-1,12-dodecamethylenediamine (compound 2) exhibited the most potent anti-melanoma activities both in vitro and in vivo.

Chemical structures of cinnamamide derivatives.

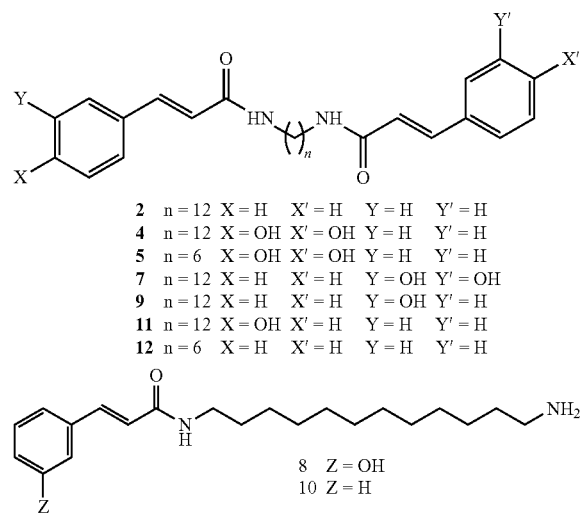

| 2  | n = 12 | X = H  | X' = H  | Y = H  | Y' = H  |
|----|--------|--------|---------|--------|---------|
| 4  | n = 12 | X = OH | X' = OH | Y = H  | Y' = H  |
| 5  | n = 6  | X = OH | X' = OH | Y = H  | Y' = H  |
| 7  | n = 12 | X = H  | X' = H  | Y = OH | Y' = OH |
| 9  | n = 12 | X = H  | X' = H  | Y = OH | Y' = H  |
| 11 | n = 12 | X = OH | X' = H  | Y = H  | Y' = H  |
| 12 | n = 6  | X = H  | X' = H  | Y = H  | Y' = H  |

8   Z = OH
10  Z = H

The compounds described herein may be administered at pharmaceutically effective dosages. Such dosages are normally the minimum dose necessary to achieve the desired therapeutic effect; in the treatment of cancer, such as melanoma, for example, this amount would be roughly that necessary to treat a cancer. Generally, such doses will be in the range 0.001-1000 mg/day, or 0.001-1000 mg/kg of body weight. However, the actual amount of the compound to be administered in any given case will be determined by a physician taking into account the relevant circumstances, such as the size and location of the tumor, the age and weight of the patient, the patient's general physical condition, and the route of administration.

Preferably, the patient will be administered a compound orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, formulations may be designed to delay release of the active compound over a given period of time, or to carefully control the amount of drug released at a given time during the course of therapy.

In another embodiment, provided are pharmaceutical compositions including at least one compound in a pharmaceutically acceptable carrier or excipient. The phrase "pharmaceutically acceptable" means the carrier, diluent or excipient must be compatible with the other ingredients of the formulation and not deleterious to the recipient thereof.

Pharmaceutical compositions can be used in the form of a solid, a solution, an emulsion, a dispersion, a micelle, a liposome, and the like, wherein the resulting composition contains one or more compounds described herein, as an active ingredient, in admixture with an organic or inorganic carrier or excipient suitable for enteral or parenteral applications. One or more compounds may be combined, for example, with the usual non-toxic, pharmaceutically acceptable excipients for tablets, pellets, capsules, suppositories, solutions, emulsions, suspensions, and any other form suitable for use. The excipients which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers or excipients suitable for use in manufacturing preparations, in solid, semisolid, or liquid form. In addition auxiliary, stabilizing, thickening and coloring agents and perfumes may be used. Compounds described herein are included in pharmaceutical compositions in an amount sufficient to produce the desired effect upon the process or disease condition.

Pharmaceutical compositions may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing compounds described herein in admixture with non-toxic pharmaceutically acceptable excipients may also be manufactured by known methods.

The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may also be in the form of a sterile injectable suspension. Suspensions may be formulated according to known methods using suitable dispersing or wetting agents and suspending agents. The sterile injectable preparations may also be sterile injectable solutions or suspensions in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Compounds described herein may also be administered in the form of suppositories for rectal administration. These compositions may be prepared by mixing the compounds with a suitable non-irritating excipient, such as cocoa butter, synthetic glyceride esters of polyethylene glycols, which are solid at ordinary temperatures, but liquefy and/or dissolve in the rectal cavity to release the drug.

Compounds described herein may also be administered in a topical form.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mardenti, J. and Chappell, W. "The use of interspecies scaling in toxicokinetics" In Toxicokinetics and New Drug Development, Yacobi et al, Eds., Pergamon Press, New York 1989, pp. 42-96. The term "therapeutically effective" amount as used herein refers to the amount needed to perform the particular treatment such as, for example, cancer. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. In a preferred embodiment, the disorder is present. In a preferred embodiment, the life of a cell or an individual is prolonged due to the methods described herein.

The compositions provided herein may be administered in a physiologically acceptable carrier to a host, as previously described. Preferred methods of administration include systemic or direct administration to a tumor cavity. In one method sustained release vehicles are utilized. The compositions may be administered in conjunction with other compositions for treatment, including but not limited to chemotherapeutics and/or radiation or with regulators thereof.

The compositions or dosage forms may contain any one of the compounds and therapeutic agents described herein in the range of 0.005% to 100% with the balance made up from the suitable pharmaceutically acceptable excipients. The contemplated compositions may contain 0.001%-100% of any one of the compounds and therapeutic agents provided herein, in one embodiment 0.1-95%, in another embodiment 75-85%, in a further embodiment 20-80%, wherein the balance may be made up of any pharmaceutically acceptable excipient described herein, or any combination of these excipients.

In some embodiments, an effective amount of the compounds and the pharmaceutically acceptable salts thereof described above, can range, for example, from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; or from about 0.1 mg/kg to about 0.5 mg/kg).

In some embodiments, an effective amount of the compound and the pharmaceutically acceptable salts thereof described above is about 0.1 mg/kg, about 0.5 mg/kg, about 1 mg/kg, about 2 mg/kg, or about 5 mg/kg.

The foregoing dosages can be administered on a daily basis (e.g., as a single dose or as two or more divided doses, e.g., once daily, twice daily, thrice daily) or non-daily basis (e.g., every other day, every two days, every three days, once weekly, twice weekly, once every two weeks, once a month).

EXAMPLES

Example 1

Materials and Methods

Trans-cinnamoyl chloride, trans-4-hydroxycinnamic acid, trans-cinnamic acid, 1,6-hexamethylenediamine, 1,12-dodecamethylenediamine, all solvents, chemicals reagents, and HPLC-eluents were purchased from Sigma-Aldrich, and used as received without further purification. Analytical HPLC was used to confirm the purity of final products (≥95%). The analytical HPLC was conducted on Shimadzu RP-HPLC system and C18 column (250 cm×4.60 mm) using water (0.1% TFA) as eluent A and acetonitrile (0.1% TFA) as eluent B, over 80 min. NMR spectra were recorded on a Bruker Avance III HD™ 400 NMR spectrometer using DMSO-d6 or $CD_3OD$ as solvents and TMS as an internal reference. Mass spectra were obtained by a Bruker Impact 11, UHR-qTOF.

CHEMICAL SYNTHESIS (2E,2'E)-N,N'-(Dodecane-1,12-diyl)bis(3-phenylacrylamide)(Bis-cinnamoyl-1,12-dodecamethylenediamine) (Compound 2)

Trans-cinnamoyl chloride (compound 1, 100 mg, 0.6 mmol) was dissolved in dry THF (15 ml), followed by adding potassium carbonate (166 mg, 1.2 mmol, 2 equiv). Solution of 1,12-dodecamethylenediamine (60 mg, 0.3 mmol, 0.5 equiv) in THF (10 mL) was added dropwise over 20 min. The reaction mixture was stirred for 4 h. After the completion of the reaction, the product was obtained as a white precipitant. The crude was collected by filtration, washed by water, and crystallized from methanol to afford compound 2 as a white solid (125 mg, 45%). The purity was confirmed by analytical HPLC ($R_t$=26.69 min).

$^1$H NMR (400 MHz, DMSO-d6): δ (ppm) 1.20-1.31 (br s, 16H, —$(CH_2)_8$—), 1.40-1.49 (m, —$CH_2$—$CH_2$—NH, 4H), 3.12-3.19 (m, —$CH_2NH_2$, 4H), 6.61 (d, J=16 Hz, —CO—CH═CH, 2H), 7.41-7.56 (m, aromatic protons, CH═CHCO, 12H), 8.19 (t, J=5 Hz, 2H, 2NH); $^{13}$C NMR (100 MHz, DMSO-d6): δ (ppm) 165.22 (2C═O), 138.79 (CH═CHCO), 135.44 (CH═CHCO), 129.82 (aromatic C), 129.39 (aromatic C), 127.92 (aromatic C), 122.85 (aromatic C), 26.90-29.60 (aliphatic $CH_2$); HR-MS (ESI-qTOF) (m/z)

[C₃₀H₄₀N₂O₂]: calcd 460.3090, found 461.3675 [M+H]+, 483.3516 [M+Na]+, and 499.3270 [M+K]+.

(2E,2'E)-N,N'-(Dodecane-1,12-diyl)bis(3-(4-hydroxyphenyl)acrylamide (Compound 4)

To a solution of 4-hydroxycinnamic acid (compound 3, 100 mg, 0.6 mmol) in DMF (20 ml) was added N-methylmorpholine (NMM, 124 µL, 1.2 mmol, 2 equiv) followed by 1-[bis(dimethylamino)methylene]-1H-1,2,3-triazolo[4,5-b]pyridinium 3-oxid hexafluorophosphate (HATU, 114 mg, 0.3 mmol, 0.5 equiv). The mixture was stirred at room temperature for 20 min, followed by adding 1,12-dodecamethylene diamine (60 mg, 0.3 mmol, 0.5 equiv). After 4 h, the solvent was evaporated, and the resulting crude solid was loaded onto silica gel and purified by chromatography, ethyl acetate:methanol as 90:10 (v/v), to provide compound 4 as a white powder (95 mg, 32%). The purity was confirmed by analytical HPLC ($R_t$=21.89 min).

$^1$H NMR (400 MHz, DMSO-d6): δ (ppm) 1.20-1.32 (br s, 16H, —(CH$_2$)$_8$), 1.37-1.48 (m, 4H), 3.10-3.19 (m, —CH$_2$NH$_2$, 4H), 6.42 (d, J=15 Hz, —CO—CH=CH, 2H), 6.78-7.37 (m, aromatic protons, CH=CHCO, 10H), 7.95 (t, J=5 Hz, 2H, 2NH), 9.81 (s, 2H, 2OH). $^{13}$C NMR (100 MHz, DMSO-d6): δ (ppm) 165.69 (2C=O), 159.21 (2C—OH), 138.89 (Alkene carbons), 129.59 (aromatic C), 126.43 (aromatic C), 119.30 (aromatic C), 116.18 (aromatic C), 26.96-29.68 (aliphatic CH$_2$); HR-MS (ESI-qTOF) (m/z) [C₃₀H₄₀N₂O₄]: calcd 492.2988, found 493.3185 [M+H]+, 515.3227 [M+Na]+, 531.2753 [M+K]+.

(2E,2'E)-N,N'-(Hexane-1,6-diyl)bis(3-(4-hydroxyphenyl)acrylamide) (Compound 5)

The synthetic procedure was the same as the one used in the synthesis of compound 4. 4-Hydroxycinnamic acid (compound 3, 100 mg, 0.6 mmol), 1,6-diaminohexane (35 mg, 0.3 mmol, 0.5 equiv), HATU (114 mg, 0.3 mmol, 0.5 equiv), and N-methylmorpholine (124 µL, 1.2 mmol, 2 equiv) were used for the synthesis. The crude product was purified by silica gel column chromatography, using ethyl acetate:methanol as 90:10 (v/v), affording a white product 5 (80 mg, 32%).

$^1$H NMR (400 MHz, DMSO-d6): δ (ppm) 1.26-1.35 (br s, 4H, —(CH$_2$)$_2$), 1.39-1.49 (m, 4H, —CH2-CH2-NH), 3.10-3.20 (m, —CH$_2$NH$_2$, 4H), 6.44 (d, J=16 Hz, —CO—CH=CH, 2H), 6.82-7.41 (m, aromatic protons, CH=CHCO, 10H), 7.99 (t, J=6 Hz, 2H, 2NH), 9.84 (s, 2H, 2OH); 13C NMR (100 MHz, DMSO-d6): 165.70 (2C=O), 159.21 (2C—OH), 138.91 (Alkene carbons), 129.60 (aromatic C), 126.43 (aromatic C), 119.30 (aromatic C), 116.10 (aromatic C), 26.60-29.70 (aliphatic CH2). HR-MS (ESI-qTOF) (m/z) [C24H28N₂O₄]: calcd 408.2049, found 409.2243 [M+H]+, 431.2371 [M+Na]+.

(2E,2'E)-N,N'-(dodecane-1,12-diyl)bis(3-(3-hydroxyphenyl)acrylamide) (Compound 7)

The synthetic procedure was the same as the one used to synthesize compounds 4 and 5. 3-Hydroxycinnamic acid was used instead of 4-hydroxycinnamic acid. In brief, 3-hydroxycinnamic acid (compound 6, 100 mg, 0.6 mmol), 1,12-dodecamethylenediamine (60 mg, 0.3 mmol, 0.5 equiv), HATU (114 mg, 0.3 mmol, 0.5 equiv), N-methylmorpholine (124 µl, 1.2 mmol, 2 equiv) were used for the synthesis. The crude product was purified by silica gel column chromatography, using ethyl acetate:methanol as 90:10 (v/v), affording a white product compound 7 (110 mg, 37%). The purity was confirmed by analytical HPLC ($R_t$=22.19 min).

1H NMR (400 MHz, CD3OD): δ (ppm) 1.23-1.36 (br s, 16H, —(CH2)8), 1.48-1.56 (m, 4H, —CH2-CH2-NH), 3.20-3.25 (m, —CH2NH2, 4H), 6.53 (d, J=15 Hz, —CO—CH=CH, 2H), 6.80-7.46 (m, aromatic hydrogens, CH=CHCO, 10H); 13C NMR (100 MHz, CD3OD): δ (ppm) 167.24 (2C=O), 157.61 (2C—OH), 140.30 (CH=CHCO), 136.25 (CH=CHCO), 120.38 (aromatic C), 118.89 (aromatic C), 116.47 (aromatic C), 113.70 (aromatic C), 39.20 (CH2NH), 26.60-29.25 (alphantic CH$_2$); HR-MS (ESI-qTOF) (m/z) [C₃₀H₄₀N₂O₄]: calcd 492.2988, found 493.3168 [M+H]+, 515.2990 [M+Na]+, 531.2733 [M+K]+.

(E)-N-(12-Aminododecyl)-3-(3-hydroxyphenyl) acrylamide (Compound 8)

3-Hydroxycinnamic acid (compound 6, 200 mg, 1.2 mmol), was added to equimolar amounts of 1,12-dodecamethylenediamine (244 mg, 1.2 mmol), (2-(1H-benzotriazol-1-yl)-1,1,3,3-tetramethyluronium hexafluorophosphate (HBTU, 455 mg, 1.2 mmol, 1 equiv), in DMF (20 ml), followed by addition of N,N-diisopropylethylamine (DIPEA, 417 µl, 2.4 mmol, 2 equiv) and stirring at RT for 3 h. The crude compound was subjected to silica gel column chromatography for purification, using ethyl acetate:methanol:ammonia as 73:25:2 (v/v/v), to give a white product (compound 8, 115 mg, 27%). The purity was confirmed by analytical HPLC ($R_t$=19.09 min).

1H NMR (400 MHz, DMSO-d6): δ (ppm) 1.20-1.35 (br s, 16H, —(CH2)8), 1.40-1.58 (m, 4H, —CH2-CH2-NH), 2.68-2.81 (m, 2H, CH2NH2), 3.10-3.21 (m, 2H, NHCH2), 6.55 (d, J=16 Hz, —CO—CH=CH, 1H), 6.76-7.32 (m, aromatic protons, CH=CHCO, 5H), 7.69 (s, 2H, NH2), 8.08 (t, J=6 Hz, 1H, NH), 9.57 (s, 1H, OH); 13C NMR (100 MHz, DMSO-d6): δ (ppm) 164.25 (2C=O), 158.17 (C—OH), 138.99 (CH=CHCO), 136.69 (CH=CHCO), 130.37 (aromatic C), 122.58 (aromatic C), 119.07 (aromatic C), 117.03 (aromatic C), 114.12 (aromatic C), 22.50-29.65 (—CH2). HR-MS (ESI-qTOF) (m/z) [C21H34N2O2]: calcd 346.2620, found 347.0936 [M+H]+.

(E)-N-(12-Cinnamamidododecyl)-3-(3-hydroxyphenyl) acrylamide (Compound 9)

The synthetic procedure was the same as the one used in synthesis of compound 5 using N-(12-aminododecyl)-3-(3-hydroxyphenyl) acrylamide (compound 8, 50 mg, 0.14 mmol), trans-cinnamic acid (compound 1, 20 mg, 0.14 mmol), HATU (27 mg, 0.07 mmol, 0.5 equiv), and N-methylmorpholine (29 µL, 0.28 mmol, 2 equiv). The crude compound was subjected to silica gel column chromatography to purify the crude product, using methylene chloride:ethylacetate as 70:30 (v/v) to yield compound 9 (35 mg, 50%). The purity was confirmed by analytical HPLC ($R_t$=23.94 min).

$_1$H NMR (400 MHz, DMSO-d$_6$): δ (ppm) 1.30-1.32 (br s, 16H, —(CH$_2$)$_8$), 1.38-1.50 (m, 4H, —CH$_2$—CH$_2$—NH), 3.09-3.20 (m, —CH$_2$NH2, 4H), 6.50 (d, J=16 Hz, —CO—CH=CH, 1H), 6.59 (d, J=16 Hz, —CO—CH=CH, 1H), 6.76-7.55 (m, aromatic protons, CH=CHCO, 11H), 8.02-8.10 (m, 2H, 2NH), 9.55 (s, 1H, OH). 13C NMR (100 MHz, DMSO-d6): δ (ppm) 165.23 (C=O), 165.22 (C=O), 158.14 (C—OH), 138.98 (CH=CHCO), 138.79 (CH=CHCO), 136.71 (CH=CHCO), 135.45 (CH=CHCO), 130.37 (aromatic C), 129.81 (aromatic C), 129.38 (aromatic C), 127.91 (aromatic C), 122.85 (aromatic C), 122.59 (aromatic C), 119.08 (aromatic C), 117.02 (aromatic C), 114.11 (aromatic C), 26.90-29.62 (aliphatic —CH$_2$); HR-MS (ESI-qTOF) (m/z) [C$_{30}$H$_{40}$N$_2$O$_3$]: calcd 476.3039, found 477.3245 [M+H]+, 499.3068 [M+Na]+.

N-(12-Aminododecyl)cinnamamide (Compound 10)

HBTU (507 mg, 1.34 mmol, 1 equiv) was added to equimolar amounts of trans-cinnamic acid (compound 1, 200 mg, 1.34 mmol) and 1,12-dodecamethylenediamine (268 mg, 1.34 mmol, 1 equiv) in DMF (20 ml), followed by addition of DIPEA (465 µL, 2.4 mmol, 2 equiv) and stirring at RT for 3 h. After completion of the reaction, the solution was evaporated. The white residue powder was subjected to silica gel column chromatography, using ethyl acetate:methanol:ammonia as 75:23:2 (v/v/v) to give the desired product compound 10 (110 mg, 25%). The purity was confirmed by analytical HPLC (R$_t$=20.28 min).

$_1$H NMR (400 MHz, DMSO-d$_6$): δ (ppm) 1.21-1.32 (br s, 16H, —(CH$_2$)$_8$), 1.39-1.55 (m, 4H, —CH$_2$—CH$_2$—NH), 2.74 (t, J=8 Hz, 2H, CH$_2$NH$_2$), 3.18 (q, J=7 Hz, 2H, NHCH2), 6.60 (d, J=16 Hz, —CO—CH=CH, 1H), 7.35-7.55 (m, aromatic protons, CH=CHCO, 6H), 7.68 (s, 2H, NH$_2$), 8.09 (t, J=6 Hz, 1H, NH); $_{13}$C NMR (100 MHz, DMSO-d$_6$): δ (ppm) 165.23 (CO), 138.79 (CH=CHCO), 135.43 (CH=CHCO), 129.83 (aromatic C), 129.39 (aromatic C), 127.91 (aromatic C), 122.88 (aromatic C), 26.20-29.70 (aliphatic —CH2); HR-MS (ESI-qTOF) (m/z) [C21H34N2O]: calcd 330.2671, found 331.3007 [M+H]+.

(E)-N-(12-Cinnamamidododecyl)-3-(4-hydroxyphenyl) acrylamide (Compound 11)

The synthetic procedure was the same as the one used for the synthesis of compound 5 using N-(12-aminododecyl)cinnamamide (compound 10, 50 mg, 0.15 mmol), 4-hydroxycinnamic acid (compound 3, 25 mg, 0.15 mmol, 1 equiv), HATU (29 mg, 0.07 mmol, 0.5 equiv), and N-methylmorpholine (23 µl, 0.28 mmol, 2 equiv). Silica gel column chromatography was used for the purification of the crude product with methylene chloride:ethyl acetate (70:30 (v/v)) as eluents to generate compound 11 as a white product (40 mg, 55%). The purity was confirmed by analytical HPLC (Rt=23.68 min).

1H NMR (400 MHz, DMSO-d6): δ (ppm) 1.15-1.33 (br s, 16H, —(CH2)8), 1.32-1.50 (m, 4H, —CH2-CH2-NH), 3.07-3.21 (m, —CH2NH2, 4H), 6.41 (d, J=16 Hz, —CO—CH=CH, 1H), 6.59 (d, J=16 Hz, —CO—CH=CH, 1H), 6.77-7.55 (m, aromatic protons, CH=CHCO, 11H), 7.92 (t, J=5 Hz, 1H, NH), 8.08 (t, J=5 Hz, 1H, NH), 9.80 (s, 1H, OH); 13C NMR (100 MHz, DMSO-d6): δ (ppm) 164.95 (C=O), 164.20 (C=O), 159.21 (C—OH), 138.88 (CH=CHCO), 138.79 (CH=CHCO), 135.45 (CH=CHCO), 129.80 (aromatic C), 129.58 (aromatic C), 127.91 (aromatic C), 126.43 (aromatic C), 122.86 (aromatic C), 119.31 (aromatic C), 116.18 (aromatic C), 23.50-29.70 (aliphatic —CH2); HR-MS (ESI-qTOF) (m/z) [C$_{30}$H$_{40}$N$_2$O$_3$]: calcd 476.3039, found 477.3203 [M+H]+, 499.3364 [M+Na]+.

(2E,2'E)-N,N'-(hexane-1,6-diyl)bis(3-phenylacrylamide) (Compound 12)

Hexane-1,6-diamine (0.58 g, 5 mmol), cinnamic acid (1.48 g, 10 mmol), and pyridine (15 mL) were mixed in a round bottom flask and stirred for about 15-20 min. Triphenyl phosphite (2.8 mL, 10.75 mmol) was added to the flask, and the reaction mixture was refluxed for 8 h. Pyridine was distilled out after cooling the mixture to room temperature to reduce the volume to 5 mL. The mixture was left for overnight standing. After acetone was added, the obtained solid product was filtered and washed with acetone. Methanol was used for the recrystallization of the crude product (1.32 g, 70%). mp 192° C.

1H NMR (400 MHz, DMSO-d6): δ 1.33 (s, 4H, CH$_2$); 1.47 (s, 4H, —CH2-CH2-NH), 4.15 (q, 4H, J=19.4 Hz, —CH2NH2), 6.63 (d, J=15.8 Hz, 2H, Olefin proton), 7.35-7.43 (m, 4H, Olefin protons and Ph-H); 7.52 (m, 8H, PhH); 8.10 (s, 2H, NH). $_{13}$C NMR (400 MHz, DMSO-d$_6$) δ 165.30 (2C=O), 138.81 (CH=CHCO), 135.42 (CH=CHCO), 129.88 (aromatic C), 129.39 (aromatic C), 127.92 (aromatic C), 122.85 (aromatic C), 39.09 (CH$_2$NH), 29.6 (—CH$_2$), 26.7 (—CH$_2$), HR-MS (ESI-qTOF) (m/z) [C$_{24}$H$_{29}$N$_2$O$_2$] calcd 376.2151, found 377.2240 [M+H]+.

Three-Dimensional Virtual Docking Using Molsoft ICM-Pro System

The in silico molecular docking was performed using Molsoft ICM (×64). The APE/Ref-1 protein (1BIX, 10.2210/pdb1BIX/pdb) was added, and the druggable binding cavity located in the redox-regulatory domain was identified. The molecular docking conformation presenting the lowest binding energy was selected to visualize the possible compound-protein interaction. The virtual docking score was collected. The lower the ICM score was, the higher the chance the ligand was a binder.

Cell Lines and Cell Culture

Human malignant melanoma cells (A375, CRL-1619™; Sk-Mel-28, HTB-72™) were purchased from ATCC®. Cells were cultured in Dulbecco's Modified Eagle Medium (DMEM) (ATCC #30-2002) or Eagles' Minimum Essential Medium (EMEM) (ATCC #30-2003) supplemented with 10% fetal bovine serum (FBS) (ATCC #30-2020) at 37° C. in 5% CO$_2$ incubator. All the cells were passaged once reaching 70-90% confluence.

Human immortal melanoblast cell lines Hermes 1, Hermes 3A, and Hermes 4A were obtained from the Wellcome Trust Functional Genomics Cell Bank. Cells were cultured in the medium as recommended containing RPMI 1640, FBS (10%), 12-O-tetradecanoyl phorbol acetate (TPA, 200 nM), cholera toxin (CT, 200 µM), human stem cell factor (hSCF, 10 ng/ml), and endothelin 1 (EDN1, 10 nM).

In Vitro Anti-Melanoma Activity Screening Using MTT Colorimetric Assay

Cell viability analysis was conducted based on bio-reduction of a tetrazolium compound [3-(4,5-dimethylthiazol-2-yl)-5-(3-carboxymethoxyphenyl)-2-(4-sulfophenyl)-2H-tetrazolium] (MTT) metabolized by alive cells. Briefly, human melanoma cells were seeded in 96-well plates overnight. Various drugs were added in serum medium at different concentrations and incubated for 72 h, and negative controls were treated with the same amounts of DMSO solution. By the end of treatment, MTT solution (1 mg/mL) in serum-free medium was added to the wells for an additional 2 h incubation. Solubilizer solution (4 mM HCl, 0.1% NP40 in isopropanol) was then added, and the absorbance was recorded at 570 nm on a plate reader (BioRad). All readings were compared with the control, which represented 100% viability. Each experiment was performed in triplicate and independently repeated at least two times.

Luciferase Assay to Determine AP-1 Transactivation Activities

3×AP1pGL3 (3×AP-1 in pGL3-basic; Addgene plasmid #40342), which contains three canonical AP-1 binding sites (TGACTCA) upstream of a minimal promoter fragment containing a TATA box in the luciferase reporter plasmid pGL3-basic. 3×AP1pGL3 was transfected to human melanoma A375 cells using Lipofectamine 2000 following the manufacturer's instructions (Invitrogen). The cells were treated with $H_2O_2$ (100 μM) for 48 h in the presence or absence of APE/Ref-1 inhibitors (10 μM) 24 h after transfection.

After different treatments, the cells were rinsed twice with phosphate-buffered saline (PBS). Cells were then scraped from the plates in PBS and pelleted for 4 min at 4° C. in a microcentrifuge at 12,000 rpm. Cell pellets were resuspended in 100 μL luciferase lysis buffer for luciferase assay as described (Promega). Luciferase activity measured in relative light units reflects the AP-1 transcription rate and was detected by a SpectraMax M5 UV VIZ Plate Reader. Cell count was conducted for normalization. All the samples were studied in duplicate, and readings were taken in triplicate. Each experiment was repeated at least two times.

In Vivo Xenograft Melanoma

The Institutional Animal Care and Use Committee approved all the animal procedures at Chapman University (IACUC #2020-1131). Male nude mice (Nu/Nu) were purchased from Charles River and were housed and maintained in the Chapman University vivarium under pathogen-free conditions. Human A375 metastatic melanoma cells were injected subcutaneously into the mouse's flank ($1\times10^6$ cells per mouse). Three days-post tumor cell injection, mice were randomized into different groups. The treatment group was injected with compound 2 (5 mg/kg/day, i.p.) for 21 days. The growth of the tumors was monitored three times a week and measured using digital Vernier calipers. The size of the tumors was calculated as tumor volume $(mm^3)=[L\times(W_2)]/2$. The mice were sacrificed at the end of the experiment.

Results

Chemistry

A series of symmetrical and unsymmetrical dicinnamoyl derivatives conjugated through hydrophobic central units of 1,12-diaminododecane and 1,6-diaminohexane were synthesized. Different bolaamphiphiles were prepared based on increasing the hydrophilicity of these compounds by adding the hydrophilic hydroxyl group to the aromatic rings and changing the hydrophobic chain length.

First, bis-cinnamoyl-1,12-dodecamethylenediamine (2) was synthesized without any hydroxyl groups by the reaction of cinnamoyl chloride (1) with 1,12-dodecamethylenediamine in dry THF in the presence of potassium carbonate as a base. The structure of the compound was confirmed by NMR and mass spectrometry. The purity was confirmed by analytical HPLC, showing a retention time $(R_t)$=26 min (Scheme 1).

Scheme 1. Synthesis of bis-cinnamoyl-1,12-dodecamethylenediamine (2)

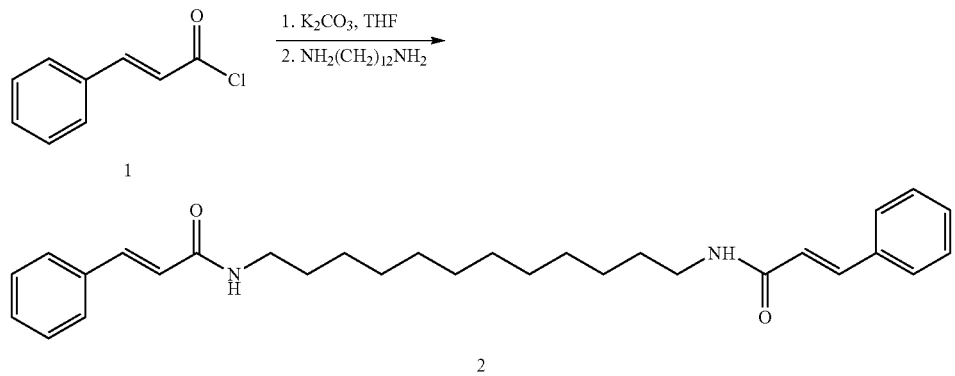

To improve the water solubility, diamide bolaamphiphiles containing two hydroxyl groups were prepared using HATU as a coupling reagent and NMM. Symmetrical bolaamphiphile derivatives (4, 5, and 7) were prepared through a coupling reaction of one equivalent of 1,12-dodecamethylenediamine with two equivalents of the cinnamic acid derivative under basic conditions. 4-Hydroxycinnamic acid (3) and 3-hydroxycinnamic (6) acid were activated by HATU, followed by coupling reaction with 1,12-dodecamethylenediamine in the presence of NMM as a basic catalyst to generate the corresponding diamide, bis-(4-hydroxy-cinnamoyl)-1,12-dodecamethylenediamine (4) and bis-(3-hydroxy-cinnamoyl)-1,12-dodecamethylenediamine (7), respectively (Schemes 2A and 2B). Analytical HPLC confirmed the purity of compounds 4 and 7, showing retention times of $(R_t)$=21.89 and 22.19 min, respectively. Moreover, to prepare a more hydrophilic bolaamphiphile derivative, a shorter aliphatic 1,6-dihexylamine was used for the reaction with 3 to prepare bis-(4-hydroxy-cinnamoyl)-1,6-hexanemethylenediamine (5) under the same conditions (Scheme 2B). The crude products were purified by silica gel column chromatography. Analytical HPLC confirmed the purity.

Unsymmetrical cinnamide derivatives 9 and 11 were synthesized in two steps. First, the reaction of equimolar amounts of the appropriate acid derivative and the diamine was used to afford the corresponding monocinamamide. It is noted that optimizing the reaction conditions, like using mild activating reagent and reaction time control, was required to drive the reaction towards only one coupling and create the desired compound containing a free amine group for the subsequent coupling. As depicted in Scheme 2, compounds N-(12-aminododecyl)-3-(3-hydroxyphenyl) acrylamide (8) and N-(12-aminododecyl)-cinnamamide (10) were constructed from the reaction of 3-hydroxycinnamic acid (6) and cinnamic acid (1), respectively, with diamine in the presence of HBTU and DIPEA for 2 h. As a representative example, the monoamide (8) was identified via mass spectrometry, exhibiting 347.0936 [M+H]+. Moreover, the $^1$H NMR spectra showed broad singlet and triplet peaks at 7.69 and 8.08 ppm, which are characteristics for NH$_2$ and NH, respectively. Besides, a singlet peak at 9.57 ppm represents the phenolic hydroxyl group.

Second, the reaction of monocinnamoyl-fatty acyl amide conjugates (8 and 10) containing free amino group with the additional cinnamic acid derivatives (1 and 3), under similar conditions used for the synthesis of 4, afforded the corresponding unsymmetrical bis-cinnamoyl derivatives containing only one hydroxyl group, N-(12-cinnamamidododecyl)-3-(3-hydroxyphenyl) acrylamide (9) and N-(12-cinnamamidododecyl)-3-(4-hydroxyphenyl) acrylamide (11), respectively (Schemes 2B and 2C). As a representative example, the $^1$HNMR spectrum fits well with the structure (9) and indicated that the molecule has unsymmetrical imide protons, showing two triplet signals at 7.92 and 8.08 ppm.

(2E,2'E)-N,N'-(Propane-1,3-diyl)bis(3-phenylacrylamide) 12 was synthesized through an alternative method. Hexane-1,6-diamine was reacted with cinnamic acid in the presence of pyridine and triphenyl phosphite for 8 h to afford compound 12 (Scheme 2D).

Scheme 2. Synthesis of symmetrical (4, 5, 7, 12) and unsymmetrical (9 and 11) bis-cinnamoyl derivatives.

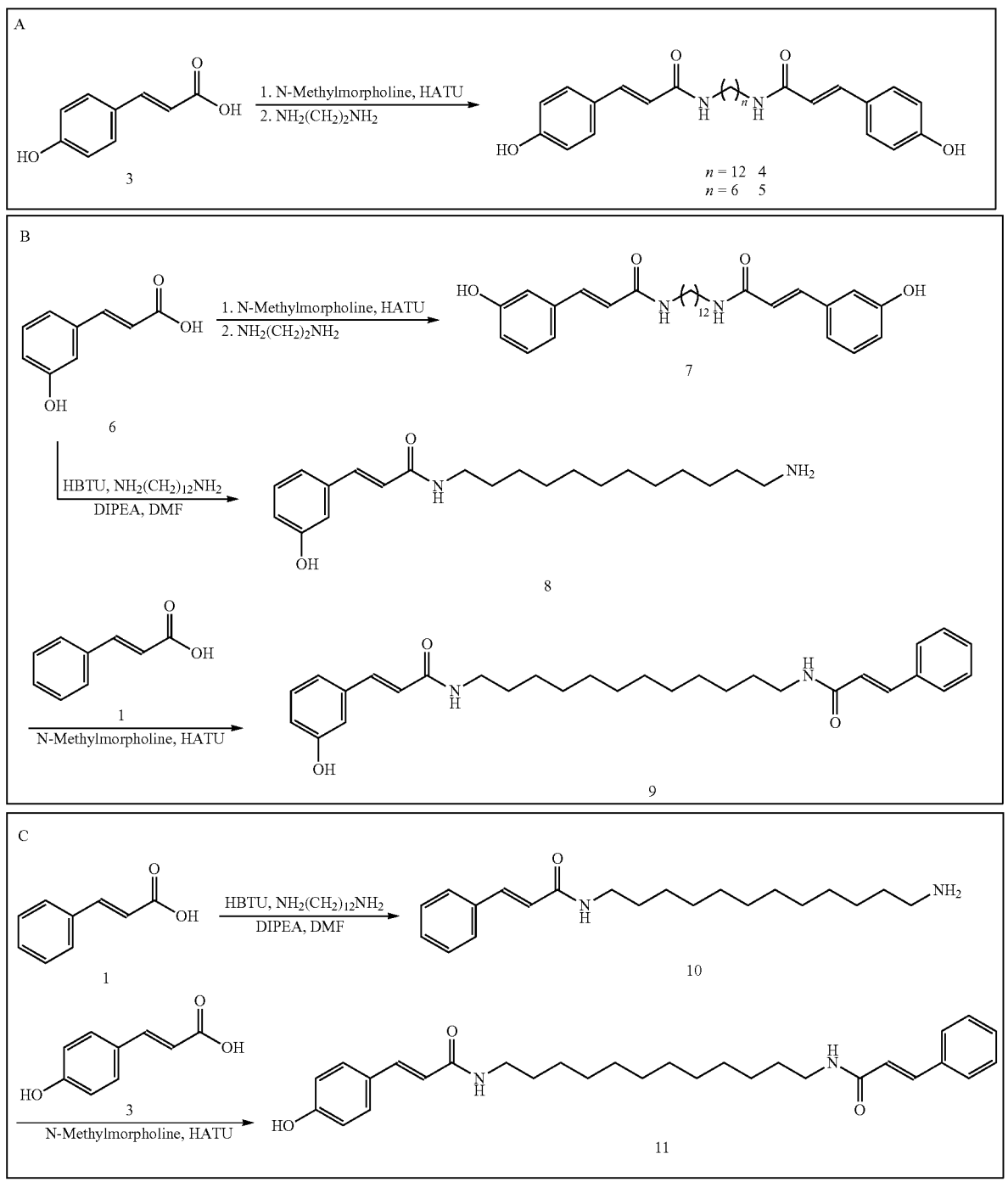

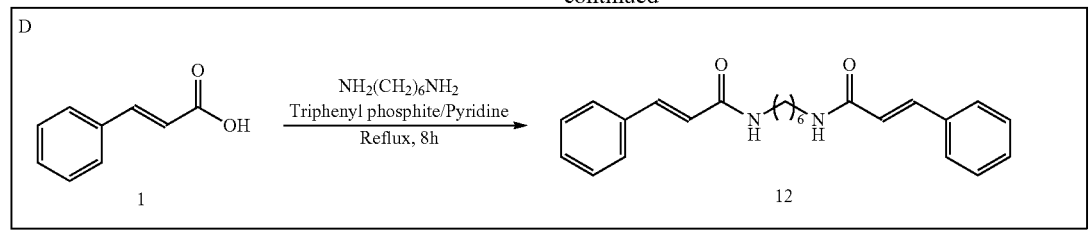

Molecular Docking Study of the Synthesized Compound Candidates

The compounds were further evaluated through molecular modeling and docking scoring against the APE/Ref-1 crystal structure, downloaded from PDB (1BIX) (Table 1). FIG. 1 showed the binding mode of compound 2 into its binding site of APE/Ref-1, resulting in an ICM docking score of −9.23. Compound 11 docked into the same binding cavity, and the ICM docking score was −16.31. The best docking score among all the synthesized candidate compounds was observed with Compound 4 (−20.14), as shown in Table 1.

Effects of APE/Ref-1 Inhibitors on Melanoma Proliferation Using MTT Colorimetric Assay Since APE/Ref-1 inhibitors have exhibited anti-proliferation and anti-angiogenesis activity against several human malignancies, anti-tumor efficacy was chosen as an endpoint to rank the candidate compounds for bio-evaluation. MTT assays were conducted to evaluate the in vitro anti-melanoma activities of the synthesized compounds in human melanoma cell lines and immortalized melanocytes. Cells were incubated with compounds at different concentrations for 72 h. Cell viabilities after treatments were then analyzed in comparison to that of control.

Figure 2A:
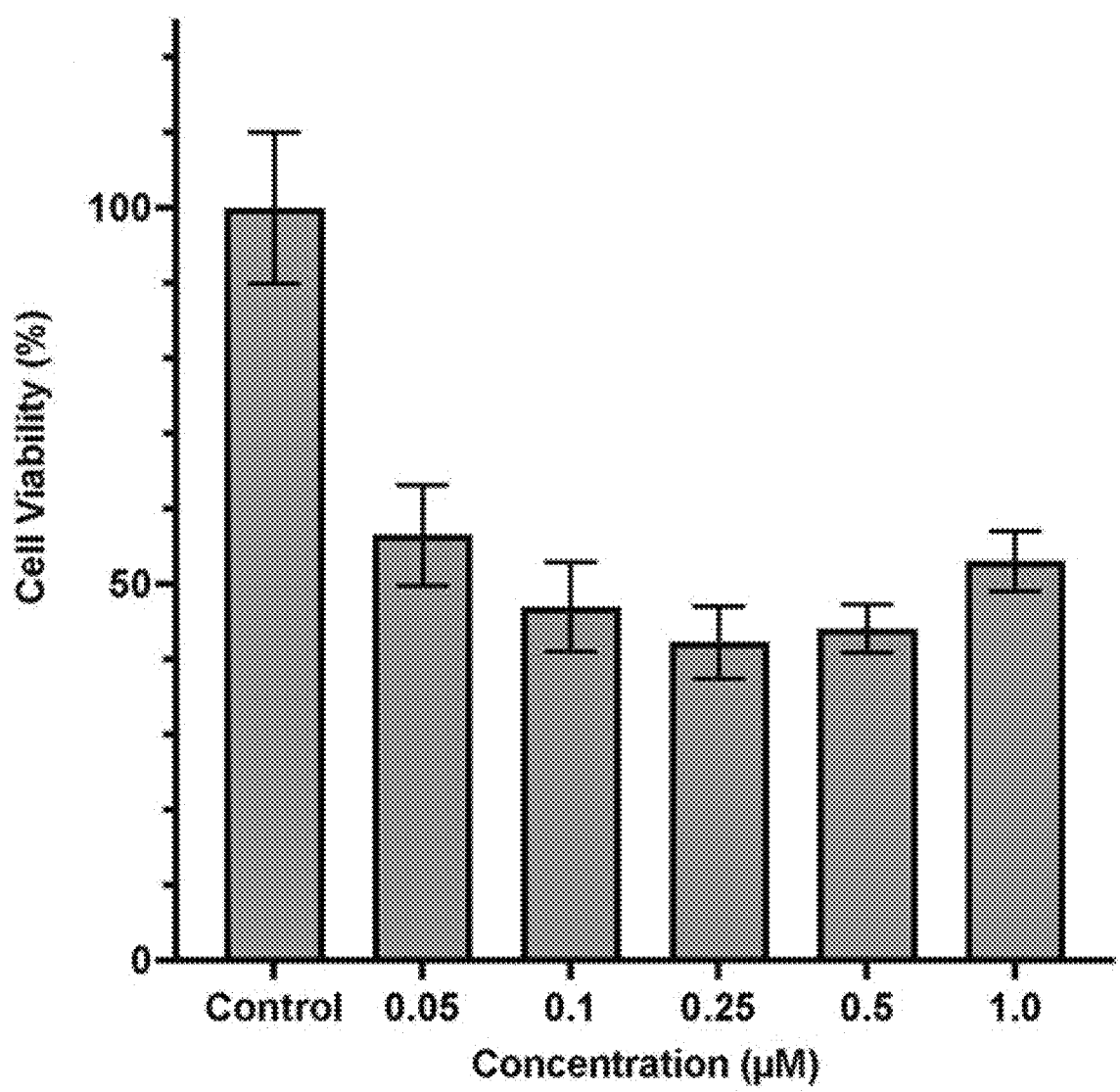
FIGS. 2A-2D. Potent cytotoxicity of compounds 2 and 11 in human melanoma cells. Cell viability was determined by MTT assay. The results are shown as the percentage of cell survival after 72 h treatment at different concentrations. The results were statistically processed from three independent experiments. The $IC_{50}$ was calculated using GraphPad Prism 8.
Figure 2B:
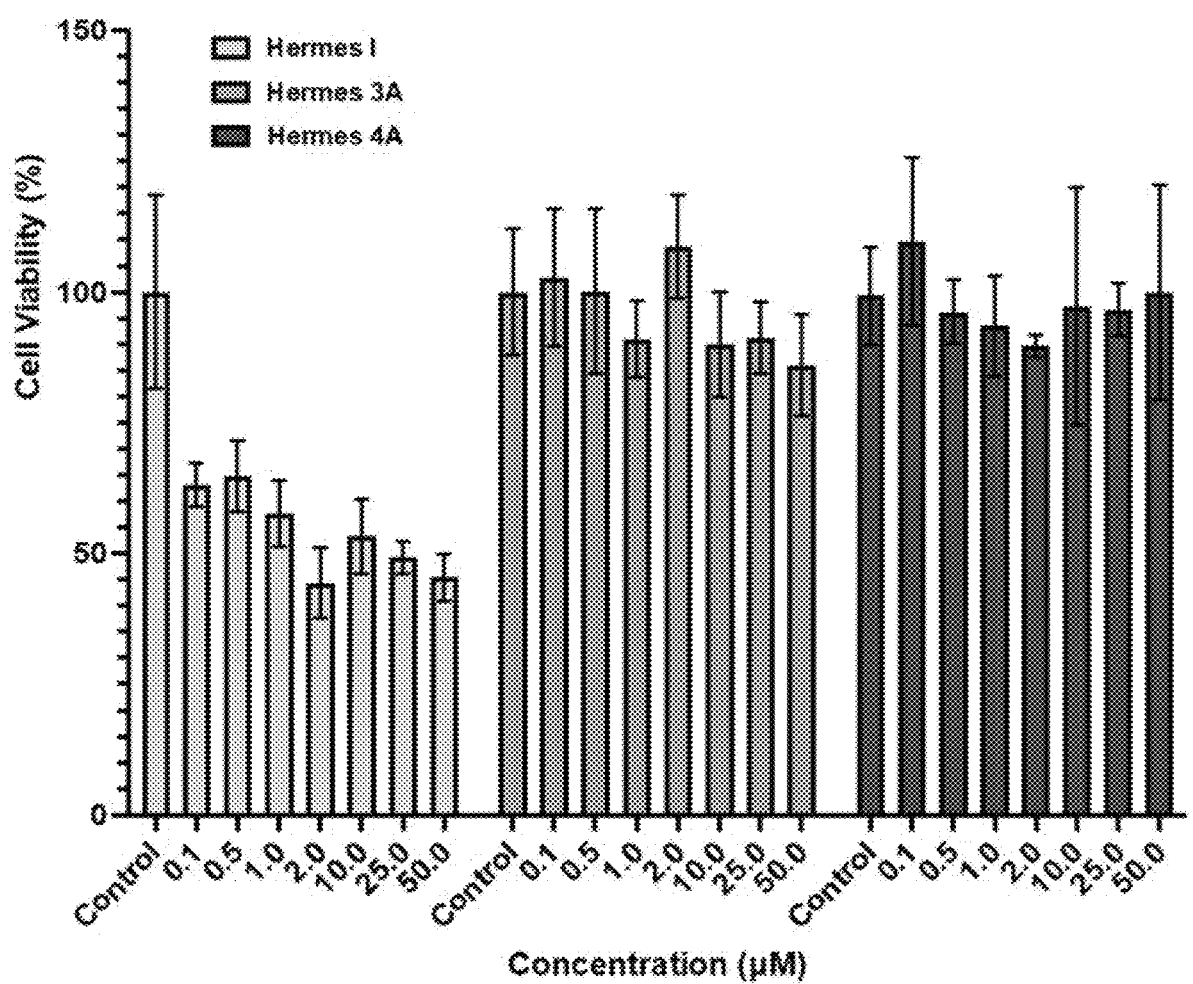

As shown in FIG. 2A, lead compound 2 exhibited potent cytotoxicity in human melanoma A375 cells at 0.1 µM as the surviving cells were reduced to less than 50% of control after 72 h treatment. However, with increasing doses, the cellular toxicity was not increased accordingly in both cell lines, which may be explained by the limited water solubility and stability of compound 2 (FIG. 2A). Apparent drug precipitation was evident in the media at higher concentrations (2.5 µM). Of note, no significant cytotoxicity of compound 2 was observed among two melanoblast cell lines after 72 h treatment (Hermes 3A and Hermes 4A, FIG. 2B). Hermes 1 cells were more sensitive to compound 2, but the cytotoxicity was not elevated with increasing the concentrations.

Compounds 4 and 7 are analogs of lead compound 2 in which two hydrophilic hydroxyl groups (—OH) were added to the aromatic rings. The Molsoft virtual docking scores of compounds 4 and 7 are −20.14 and −11.74, respectively. Compared to compound 2 (−9.23), compound 4 docks better to the druggable pocket localized in the redox domain of APE/Ref-1. However, the MTT results showed these modifications led to a significant loss of anti-tumor activity compared to compound 2.

Compound 5 has two hydrophilic groups (—OH) like compound 4 but includes a modified chain length to increase the water solubility. The virtual docking score of compound 5 is −12.91. MTT analysis demonstrated that such modification also resulted in the loss of anti-melanoma activity compared to compound 2, and $IC_{50}$ was not observed up to 50 µM (Table 1).

Compounds 9 and 11 are the analogs of lead compound 2, in which one hydrophilic hydroxyl group (—OH) was added to the meta- or para-position accordingly. The virtual docking scores of compounds 9 and 11 are −5.97 and −16.31, respectively (Table 1). Compound 9 showed poor anti-melanoma activity, while compound 11 exhibited a potent cytotoxic effect in melanoma cells (FIG. 2). The virtual docking profile aligns well with their anti-melanoma activities, suggesting the position of the —OH group plays a vital role in their interaction with the APE/Ref-1 protein. Moreover, compound 11 exhibits improved water solubility and stability compared to compound 2 with the hydrophilic hydroxyl group. The significant precipitation was evident at ~20 µM concentration, approximately 8-folds higher than compound 2 (2.5 µM).

TABLE 1

Docking scores and cytotoxicity of the compound in human melanoma A375 and SK-Mel-28 cells.

| Synthesized Compounds | Chemical formula | Docking Score | Anti-melanoma Activities |
|---|---|---|---|
| Compound 2 | $C_{30}H_{40}N_2O_2$ | −9.23 | Cytotoxicity is not dose-dependent; at 0.1 µM, cell viability reduced to <50% of control in A375 cells. |
| Compound 11 | $C_{30}H_{40}N_2O_3$ | −16.31 | 0.079 ± 0.013 µM ($IC_{50}$, detected by MTT assay, average in two human melanoma cell lines: A375 and SK-Mel-28) |
| Compound 4 | $C_{30}H_{40}N_2O_4$ | −20.14 | 50% inhibition of cell survival not observed up to 10 µM. |
| Compound 5 | $C_{24}H_{28}N_2O_4$ | −12.91 | 50% inhibition of cell survival was not observed up to 50 µM. |
| Compound 7 | $C_{30}H_{40}N_2O_4$ | −11.74 | 50% inhibition of cell survival not observed up to 10 µM. |
| Compound 8 | $C_{21}H_{34}N_2O_2$ | −12.51 | 50% inhibition of cell survival not observed up to 25 µM. |
| Compound 9 | $C_{30}H_{40}N_2O_3$ | −5.97 | 50% inhibition of cell survival not observed up to 10 µM. |
| Compound 10 | $C_{21}H_{34}N_2O$ | −15.44 | 50% inhibition of cell survival not observed up to 25 µM. |
| Compound 12 | $C_{24}H_{28}N_2O_2$ | −10.06 | 50% inhibition of cell survival not observed up to 10 µM. |

Potent and Selective Anti-Tumor Activities of Compound 11 in Human Melanoma Cells.

Figure 2C:
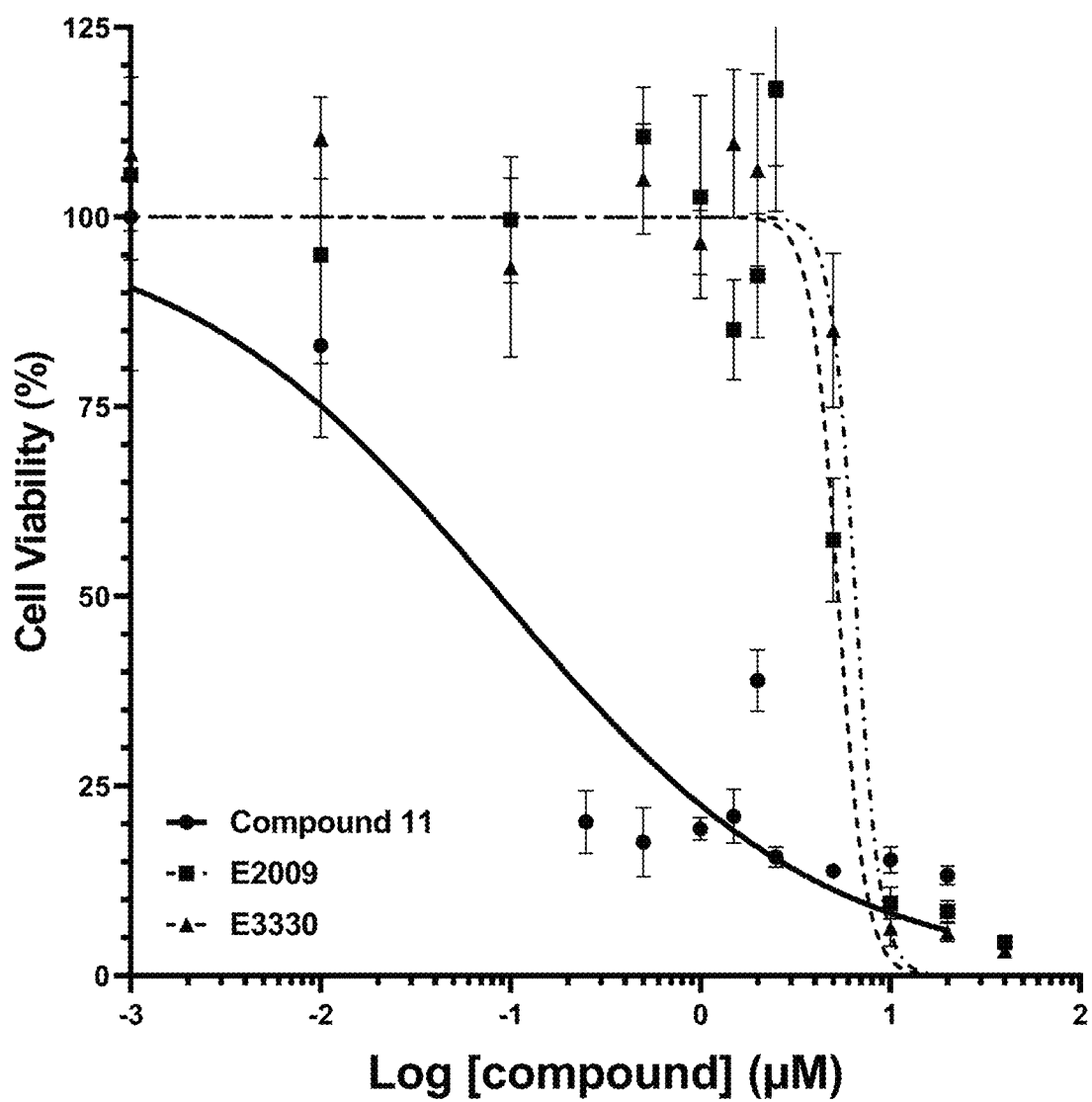
Figure 2D:
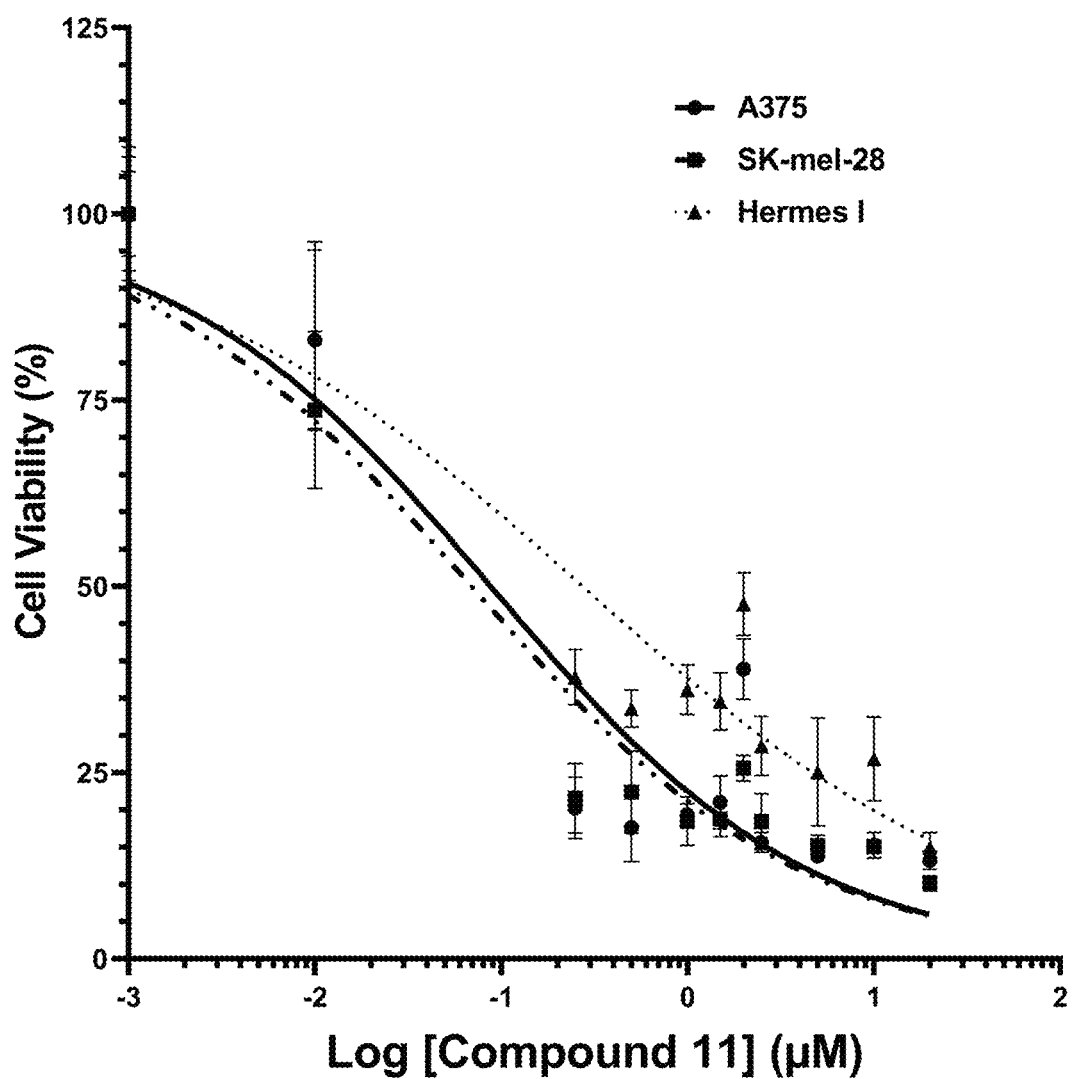

Among all the synthesized analogs of compound 2, compound 11 exhibited promising anti-tumor activities with improved water solubility in a dose-dependent manner. The viabilities of melanoma cells were significantly decreased after compound 11 treatment (FIGS. 2C-2D). In comparison to other well-studied APE/Ref-1 inhibitors E2009 and E3330, compound 11 exhibited significantly increased potency in reducing melanoma viability in melanoma cells (FIG. 2C). The $IC_{50}$s of compound 11 in A375 and Sk-Mel-28 melanoma cells were 0.088 µM and 0.07 µM, respectively (FIG. 2D), which are more potent than APE/Ref-1 inhibitors E2009 and E3330. At 1 µM, cell viability reduced to 19% of control cells (vehicle only, 0.1% DMSO) after treatment with compound 11, while no significant cytotoxicity was observed with E2009 and E3330 treatment at the same concentration (96.7% and 102.6% of control, respectively) (FIG. 2C).

The selectivity of compound 11 was also determined by comparing its cytotoxicity in melanoma cells to that in melanoblast cells. As shown in FIG. 2D, the $IC_{50}$ of compound 11 in Hermes 1 was 0.274 µM, much higher than $IC_{50}$s observed in A375 and SK-Mel-28 cells.

APE/Ref-1 Inhibitor Suppressed $H_2O_2$-Induced AP-1 Transactivation in Melanoma Cells.

Figure 3:
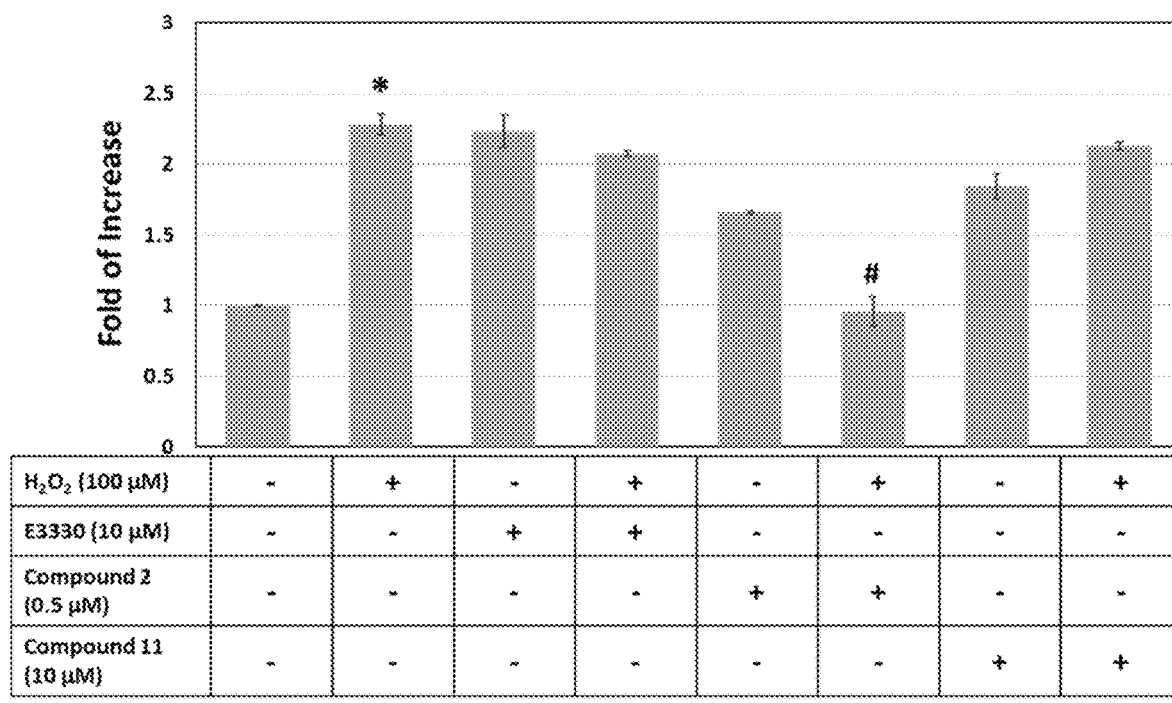
FIG. 3. Inhibition of AP-1 transcriptional activation in human melanoma A375 cells by compound 2. A375 cells were transfected with an AP-1 luciferase reporter plasmid. 24 h after transfection, cells were incubated with $H_2O_2$ (100 µM) in the presence or absence of compound 2 (0.5 µM) or compound 11 (10 µM) or E3330 (10 µM) for 48 h. After treatments, the cells were harvested to determine the luciferase activity, expressed as a fold of control without any treatment. The results normalized by cell numbers represent means±S.D of triplicates. *, $p<0.05$ compared to control; **, $p<0.05$ compared to $H_2O_2$-treatment.

An AP-1 transactivation assay was conducted in melanoma cells transfected with a luciferase reporter construct. The present disclosure showed that compound 2 at 0.5 µM effectively inhibited AP-1 transactivation induced by $H_2O_2$ in A375 melanoma cells compared to $H_2O_2$ (p<0.05) (FIG. 3). The $H_2O_2$-activated AP-1 activity was reduced from 2.3-fold of control to approximately the basal level (95.7% of control). However, compound 2 did not display any inhibition on the basal AP-1 dependent transcription. Co-treatment with E3330, an APE/Ref-1 redox inhibitor at 10 µM concentration, only reduced the AP-1 activity marginally, which was not statistically significant. Compound 11 at 10 µM also failed to inhibit $H_2O_2$-activated AP-1 transactivation (p>0.05).

In Vivo Xenograft Melanoma

Figure 4:
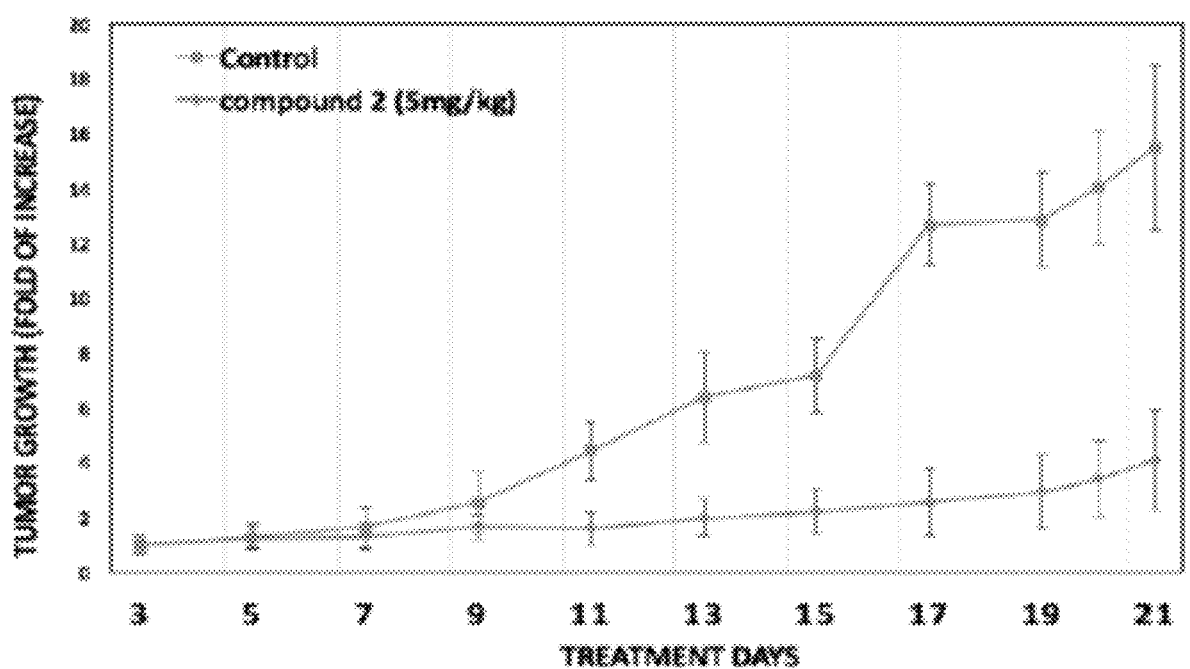
FIG. 4. Compound 2 inhibited the tumor growth of human melanoma in vivo. Metastatic melanoma A375 cells were injected into male nude mice subcutaneously on the flank. Compound 2 was administered i.p. daily at the dose of 5 mg/kg. The growth of the tumor was measured daily, and tumor volume was measured by digital calipers and determined using the formula $(mm^3)=[L\times(W2)]/2$. Tumor growth was presented as a fold of increase in size (mean±SD). *, $p<0.05$ compared to control (N=7; Compound 2 group, N=5).

Given the limited water solubility, lead compound 2 (in DMSO) was further diluted in normal saline, the drug suspension, and sonicated at room temperature for 15 min. before injection to nude mice. HPLC analysis shows no evidence of chemical structural change after compounding. The drug suspension was made fresh daily and injected into mice immediately after the compounding. As shown in FIG. 4, the study demonstrated that APE/Ref-1 inhibitor compound 2 effectively inhibited tumor growth in vivo. The effective dosage of compound 2 was as low as 5 mg/kg i.p. daily without producing any apparent systemic toxicities. After 21-day treatment, tumor size reduced to 44.7% of control (p<0.05).

In recent years, there have been dramatic developments in the treatment of advanced cutaneous melanoma (CM) using immunotherapy, which is a powerful new approach yielding remarkable and durable responses in melanoma patients. However, these checkpoint inhibitors are mainly indicated for patients with metastatic melanoma and disease progression following other treatments. In addition, current approaches have not slowed the worldwide melanoma epidemic, and the incidence of CM continues to rise in the United States. As such, the development of therapeutic interventions to block melanomagenesis and disease progression to advanced stages will have both high impact and importance.

It has been well studied that APE/Ref-1 serves as an important mechanism facilitating cancer cell survival from oxidative stresses associated with radiation therapy and chemotherapy. Certain APE/Ref-1 inhibitors have been shown to inhibit cancer cell metastasis and the development of drug resistance, suggesting that targeting APE/Ref-1 is a promising strategy to achieve a better clinical benefit for cancer patients.

In recent years, increasing efforts have been devoted to developing redox inhibitors of APE/Ref-1 for cancer treatment. However, only a limited number of compounds exhibit promising APE/Ref-1 inhibitory effects (Bapat A et al. J Pharmacol Exp Ther. 2010; 334(3):988-98; Luo M et al. Anticancer Res. 2004; 24(4):2127-34; Madhusudan S et al. Nucleic Acids Res. 2005; 33(15):4711-24). CRT0044876, which binds to the active site of APE/Ref-1, effectively inhibits its AP endonuclease activities. However, the study showed that CRT0044876 alone exhibited no toxicity to HT1080 cells up to 400 µM. CRT0044876 synergistically enhanced the cytotoxicity of methyl methanesulphonate, which was only evident at high concentrations (200 µM). Distinct from CRT0044876, a small molecule (PNRI-299) was identified as a selective inhibitor of AP-1 transcription activation mediated by APE/Ref-1. Neither toxicity nor synergistic effects were observed in the inventors' tested melanoma cell lines up to a 100 µM concentration of this compound. To date, the most successful APE/Ref-1 inhibitor reported is E3330 (APX3330) and its analogs, which exhibited therapeutic effects on tumor angiogenesis and growth without interfering with its DNA repair activities. E3330 was also shown to reduce the collective cell migration of human breast cancer cells and decrease chemo-invasion and colony formation when combined with docetaxel. However, such inhibitory activity was only evident at a higher concentration (50 µM). A recent Phase I trial of E3330 reported that six of nineteen cancer patients had disease stabilization for ≥4 cycles after treatment (Shadha S et al. Journal of Clinical Oncology. 2019; 37(15_suppl):3097). One melanoma patient presented with stable disease with 245 days of treatment.

Beyond these studies, there has been little work on structure-based inhibitor design. The redox function of APE/Ref-1 plays a vital role in melanoma progression, which is also consistent with other groups' observation of the anti-tumor activity of APE/Ref-1 redox inhibitors. The structure of the redox domain of APE/Ref-1 was therefore selected for screening and molecular modeling. In the present disclosure, first, a virtual screening using the ICM software package (MolSoft LLC) was conducted. The program uses an energetic scoring function to carry out virtual docking of molecules from a large database and ranks binding. Notably, the software incorporates ligand flexibility. Using the ICM database, over 3-million compounds were screened and the top-ranked candidate compounds were identified. After cell-based bioactivity screening, the lead APE/Ref-1 inhibitor compound 2 was successfully developed for further structure-activity study.

More analogs of compound 2 were synthesized to develop the structure-activity relationship and improve the physico-chemical properties. The present disclosure demonstrated that incorporating 1 or 2 hydroxyl groups on the aromatic ring enhances the water solubility, but this comes at the expense of reducing anti-melanoma activity. One of the synthesized compounds, compound 11, was found to be more water-soluble than compound 2 and exhibited promising anti-melanoma activities compared to the reported APE-Ref-1 inhibitors, E3330 and E2009. Anti-melanoma activities were evident even at a very low concentration (<0.1 µM). In vivo experiments showed that compound 2 treatment significantly inhibited tumor growth in a melanoma xenograft mouse model.

However, given the hydrophobic nature of compound 2, its water solubility is limited, and increased precipitation was evident once the dilution concentration was higher than 2.5 µM. Shortening the chain from C12 to C6 markedly improved the compound's water solubility, but it also significantly reduced the anti-melanoma activity. Without being bound by theory, one hypothesis is that the long chain may contribute to the binding by facilitating or stabilizing the interaction between the compound and the APE/Ref-1 protein. Shortening the chain may lead to an unstable binding profile and subsequent reduction of anti-tumor activity.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of treating melanoma in a subject comprising administration of an apurinic/apyrimidinic endonuclease 1/Redox Factor-1 (APE/Ref-1) inhibitor to the subject, the APE/Ref-1 inhibitor having the structure of Formula I:

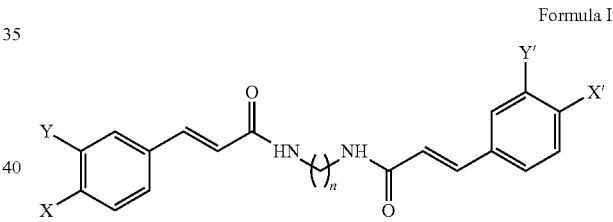

Formula I or a pharmaceutically acceptable salt thereof,
wherein n is an integer from 6 to 12,
X and X' are each independently H or OH, and
Y and Y' are each independently H or OH.

2. The method of claim 1, wherein n is 6.
3. The method of claim 1, wherein n is 12.
4. The method of claim 1, wherein n is 12, X is H, X' is H, Y is H, and Y' is H.
5. The method of claim 1, wherein n is 12, X is OH, X' is OH, Y is H, and Y' is H.
6. The method of claim 1, wherein n is 6, X is OH, X' is OH, Y is H, and Y' is H.
7. The A method of claim 1, wherein n is 12, X is H, X' is H, Y is OH, and Y' is OH.
8. The method of claim 1, wherein n is 12, X is H, X' is H, Y is OH, and Y' is H.
9. The method of claim 1, wherein n is 12, X is OH, X' is H, Y is H, and Y' is H.
10. The method of claim 1, wherein n is 6, X is H, X' is H, Y is H, and Y' is H.
11. A method of treating melanoma in a subject comprising administration of an apurinic/apyrimidinic endonuclease 1/Redox Factor-1 (APE/Ref-1) inhibitor to the subject, the APE/Ref-1 inhibitor having the structure of Formula II:

Formula II

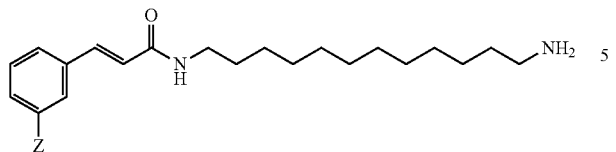

or a pharmaceutically acceptable salt thereof,
wherein Z is H or OH.

12. The method of claim 11, wherein Z is OH.

13. The method of claim 11, wherein Z is H.

14. A method of treating melanoma in a subject comprising administration of a pharmaceutical composition to the subject, the pharmaceutical composition comprising:
a compound having the structure of Formula I:

Formula I

or a pharmaceutically acceptable salt thereof,
wherein n is an integer from 6 to 12,
X and X' are each independently H or OH, and
Y and Y' are each independently H or OH; or
a compound having the structure of Formula II:

Formula II

or a pharmaceutically acceptable salt thereof,
wherein Z is H or OH; or
a combination thereof; and
a pharmaceutically acceptable carrier.

15. The method of claim 14, wherein the composition is administered topically.

16. The method of claim 14, wherein the composition is administered systemically.

* * * * *